(12) United States Patent
Zocher

(10) Patent No.: US 7,994,383 B2
(45) Date of Patent: Aug. 9, 2011

(54) WOUND GUARD BANDAGE

(75) Inventor: Marc Zocher, Bainbridge Island, WA (US)

(73) Assignee: Biosara Corporation, Bainbridge Island, WA (US)

( * ) Notice: Subject to any disclaimer, the term of this patent is extended or adjusted under 35 U.S.C. 154(b) by 0 days.

(21) Appl. No.: 12/554,050

(22) Filed: Sep. 4, 2009

(65) Prior Publication Data

US 2010/0069812 A1     Mar. 18, 2010

Related U.S. Application Data

(63) Continuation of application No. 11/318,362, filed on Dec. 23, 2005, now Pat. No. 7,605,299.

(51) Int. Cl.
*A61F 13/00*     (2006.01)

(52) U.S. Cl. ............... 602/58; 602/42; 602/48; 602/54; 128/888; 128/889

(58) Field of Classification Search ............ 602/41–59, 602/5–8, 75, 76; 128/888, 889; D24/189
See application file for complete search history.

(56) References Cited

U.S. PATENT DOCUMENTS

| 432,798 | A | * | 7/1890 | Hirst | 604/308 |
|---|---|---|---|---|---|
| 4,212,296 | A | * | 7/1980 | Schaar | 602/42 |
| 4,285,338 | A | * | 8/1981 | Lemelson | 602/58 |
| 4,667,666 | A | * | 5/1987 | Fryslie | 128/888 |
| 4,726,364 | A | * | 2/1988 | Wylan | 602/44 |
| 4,972,829 | A | * | 11/1990 | Knerr | 602/52 |
| 5,181,905 | A | * | 1/1993 | Flam | 602/41 |
| 5,386,835 | A | * | 2/1995 | Elphick et al. | 128/846 |
| 6,005,159 | A | * | 12/1999 | Spier | 602/42 |
| 6,107,536 | A | * | 8/2000 | Dadinis | 602/41 |
| 6,812,374 | B1 | * | 11/2004 | Wood | 602/41 |
| 7,265,256 | B2 | * | 9/2007 | Artenstein | 602/42 |
| 7,605,299 | B2 | * | 10/2009 | Zocher | 602/58 |

* cited by examiner

*Primary Examiner* — Kim M Lewis

(57) ABSTRACT

A disposable bandage for covering a wound area of a skin surface includes a self adhesive first fastener portion and a second fastener portion, a dome having a generally rectilinear shape and constructed from a thin rigid material, the dome being coupled to the first fastener portion along one edge and coupled to the second fastener portion along a second edge. The dome includes pleats that extend across the dome shape from the top edge to the bottom edge of the dome. A gasket is formed of a stretchable material and extends around the underside of the dome. The gasket is held in contact with the skin surface when the first fastener portion and the second fastener portion are pressed to a user's skin and, when the first fastener portion and the second fastener portion are moved away from each other, the pleats are unfolded and the gasket material is stretched and remains in contact with the skin surface.

24 Claims, 16 Drawing Sheets

WOUND GUARD BANDAGE

CROSS-REFERENCE TO RELATED APPLICATIONS

The present invention is a continuation of and claims priority from patent application Ser. No. 11/318,362, titled WOUND GUARD BANDAGE, filed on Dec. 23, 2005, the entire contents of which are incorporated by reference herein.

BACKGROUND OF THE INVENTION

1. Field of the Invention

The present invention relates generally to bandages for covering wounds and, more particularly, to bandages with protective structures that shield wounds from further injury and promote healing.

2. Description of the Related Art

Bandages are used to provide protection for wounds, cuts, incisions, abrasions, and other injuries to the skin, herein referred to as wound areas. Bandages generally cover a wound area to keep the underlying injured tissue from dirt, contaminants, and abrasions that might dislodge healing tissue or expose the healing tissue to foreign matter that would otherwise impede the natural progress of healing. In this way, bandages enhance the healing process while attempting to shield the injured tissue.

Some types of disposable bandages comprise a gauze-like pad and an adhesive tape strip that extends over the gauze pad so that the adhesive tape extensions can secure the bandage against the skin and cover the wound. When the gauze pad becomes worn or soiled, or when the underlying wound is healed, the bandage can be pulled off and discarded. Unfortunately, the healing tissue can sometimes become entangled with the gauze pad and can result in difficulties or even re-injury when the bandage is removed.

Although the disposable bandage is quite convenient and promotes healing, most disposable bandages provide very little in the way of a reasonably sterile environment for the wound area. Dirt and liquids can pass around and beneath the adhered gauze pad of the disposable bandage and can contaminate the wound area, thereby impeding the healing process. In addition, many bandages do little to protect the wound area from physical impact and abrasions. Such impacts and abrasions can be encountered with everyday activities, including activities such as simply dressing oneself or moving about during the day. Such impacts and abrasions can be very painful, and can even result in damage to the healing tissue. Moreover, many bandages cannot accommodate movement of joints and limbs to protect wound areas. That is, when many disposable bandages are applied to a wound area of a person, simple movement of limbs or joints can destroy any semblance of a sterile environment offered by the adhesive bandage, because the gauze pad tends to be lifted away from the skin when limb movement occurs. The lifting away from the skin allows penetration by outside contaminants and even water, which by itself can impede the healing process.

The description above indicates there is a need for disposable bandages that provide protection for wounds, cuts, incisions and abrasions, and that can accommodate limb and joint movement and also serve as a shield for the wound area. The present invention satisfies this need.

SUMMARY

A disposable bandage for covering a wound area of a skin surface includes a first fastener portion and a second fastener portion, each having an underside surface provided with an adhesive, a dome structure having a generally rectilinear shape and constructed from a rigid material that is constructed to provide flex. The rectilinear shape of the dome structure has a first side edge, a second side edge, a top edge, and a bottom edge, and the dome is coupled to the first fastener portion along the first side edge and coupled to the second fastener portion along the second side edge. The rigid material of the dome structure includes pleats that extend across the dome shape from the top edge to the bottom edge of the dome. A gasket is formed of a stretchable material and extends around the underside of the first side edge, top edge, second side edge, and bottom edge of the dome structure. The gasket is held in contact with the skin surface when the skin adhesive of the first fastener portion and the second fastener portion are removably adhered to a user's skin and, when the first fastener portion and the second fastener portion are moved away from each other, the pleats are unfolded and the gasket material is stretched and remains in contact with the skin surface. In this way, the disposable bandage provides protection for wounds and can accommodate limb and joint movement.

In one aspect of the bandage, the gasket provides a generally sterile environment for the underlying wound area. The pleats allow the dome structure to expand and flex with movement of limbs and joints, thereby maintaining the sterile environment provided by the gasket seal. The dome can be constructed of a vapor permeable material so that airflow can be permitted over the wound area, but liquid passage is prevented. In this way, the healing process is not likely to be compromised by physical impacts and abrasions, and a reasonably sterile environment can be provided in which the healing progress can take place, resulting in faster healing and freedom from painful impacts and abrasions from everyday activities. The dome can be constructed from a variety of materials, such as an opaque material, or a clear material for viewing the wound site, or a material that changes appearance for indicating infection, or a combination of materials.

Other features and advantages of the present invention should be apparent from the following description of the preferred embodiment, which illustrates, by way of example, the principles of the invention.

DETAILED DESCRIPTION

Figure 1:
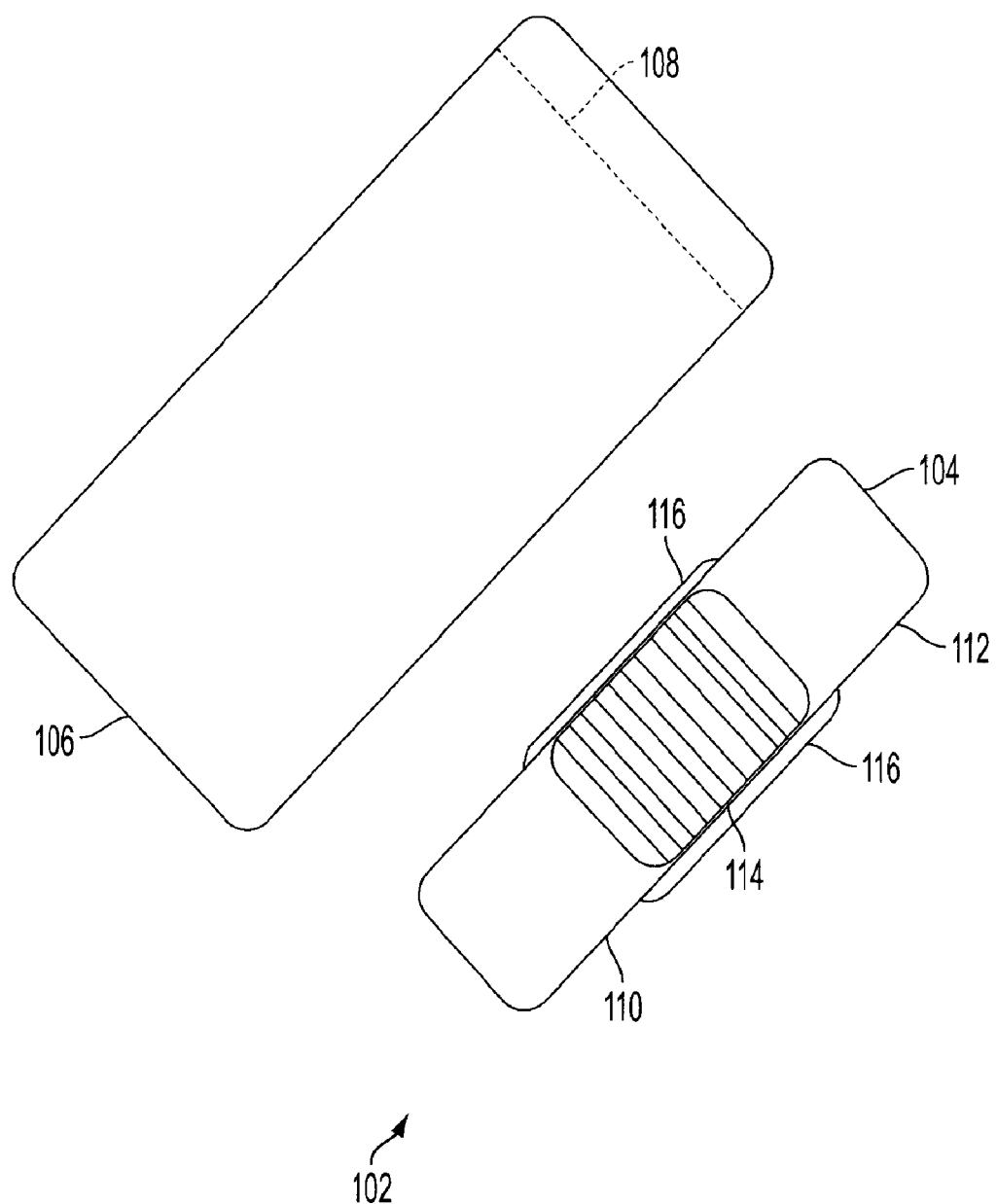
FIG. 1 is a perspective view of a wound guard bandage and container packet embodiment that are constructed in accordance with the present invention.

FIG. 1 is a perspective view of a disposable bandage product 102 embodiment constructed in accordance with the present invention, comprising a wound guard bandage 104 and packaging 106. The wound guard bandage 104 is enclosed within the packet 106 until the bandage is to be used, at which time the packet 106 is opened and the bandage is removed. For removal, the packet can be provided with a scored section 108 or other construction that can be easily torn away to open the packet and permit the bandage to be withdrawn and applied to the skin. The bandage 104 promotes healing of a wound area by providing a reasonably sterile environment around the wound area, keeping out liquid and contaminants, protecting the wound area from physical impact and abrasions, and facilitating the flow of air to the skin surface of the wound area. The product 102 can be easily transported but yet the bandage 104 is maintained sterile in the packet 106 until use, The wound guard bandage 104 includes a first fastener portion 110 and a second fastener portion 112 that are attached laterally to a dome structure 114. A gasket 116 is provided around the underside of the dome structure. The first and second fastener portions 110, 112 are provided with a self-adhesive coating on their underside, as with conventional disposable self-adhesive bandage products, so that the self adhesive coatings can be pressed against the skin surface and be removably fastened to the skin adjacent a wound area. When the adhesive portions of the bandage 104 are pressed taut to the skin, the gasket 116 is likewise pressed against the skin, and provides a sterile seal against the passage of liquid, dirt, and contaminants to the wound area.

The packaging 106 can comprise a foil pack or similar packet that can receive the bandage 104. Thus, the packet 106 can be conveniently carried about in a pocket or purse without danger of breaking or contaminating the bandage. The bandage can be produced in different sizes according to the size of the wound area it is to protect. The packaging can be configured to readily indicate different sized bandages. For example, blue packaging can be used for bandages up to a given size, and other sizes can be placed in red packaging, or green packaging, and so forth. Other product distinctions can be indicated by color coding of the packet in addition to legends or labeling. For example, as described further below, different embodiments of the bandage can be provided with medication or topical lotions. Color coding can be used to indicate medicated and non-medicated versions. Other product differences can be indicated by packet distinctions, as desired.

Figure 2:
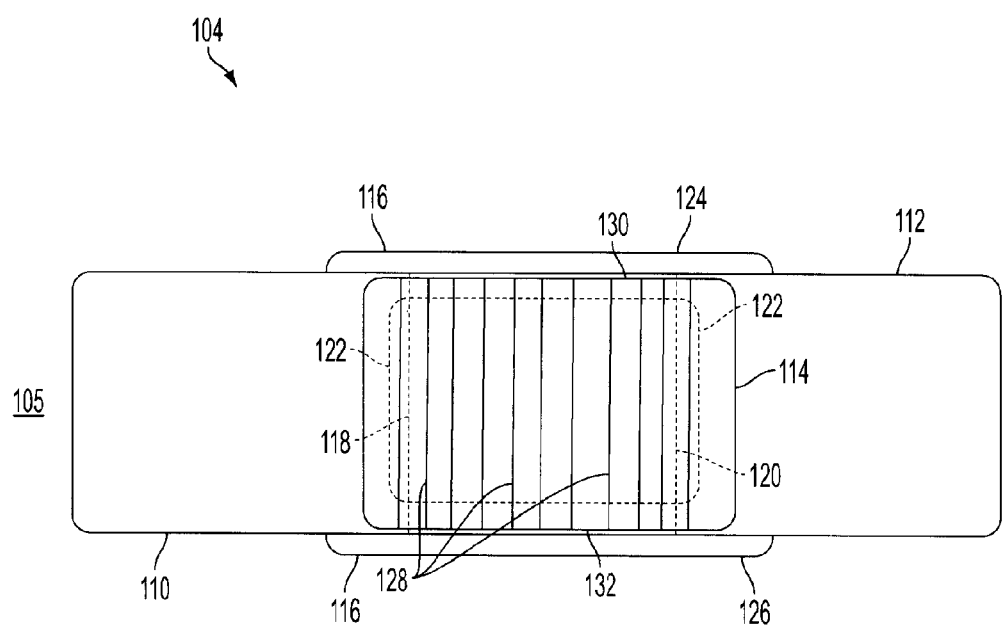
FIG. 2 is a top view of the FIG. 1 bandage in its contracted state.

FIG. 2 is a detailed top view of the bandage 104 placed over a wound area (not visible in FIG. 2) of a skin surface 105. FIG. 2 shows the top surface of the bandage, with the first fastener portion 110 right-most edge indicated by a dashed line 118 and the second fastener portion 112 left-most edge indicated by a dashed line 120. The edges of the fastener portions are not otherwise visible in the top view because the dome structure 114 is attached to the first and second fastener portion ends, thereby obscuring their respective edges in the top view. The interior edge or rim of the gasket 116 on the underside of the bandage 104 is indicated by a dashed line 122, to indicate the width of the gasket. The top 124 and bottom 126 edges of the gasket 116 are visible extending out from beneath the dome structure 114 and fastener portions 110, 112.

FIG. 2 shows that the dome structure 114 includes pleats 128 or folds that give the dome structure its combination of rigidity and flexibility. In FIG. 2, only a few of the pleats are identified with a reference numeral 128, for simplicity of illustration, but it should be apparent that the pleats extend transversely across the dome structure in FIG. 2 from the top edge 130 of the dome to the bottom edge 132 of the dome, and are provided substantially along the lateral length of the dome structure 114. The dome structure is constructed from a thin rigid material, such as plastic or dense paperboard. When the bandage 104 is removed from the packet 106, the pleats are in a compressed state, folded up, for compact storage. The FIG. 2 illustration shows the pleats 128 in the compressed condition. When the bandage is placed on the skin 105, the pleats permit the dome structure to have sufficient flexibility to stretch, becoming unfolded or deployed, and thereby move with movement of joints or limbs while maintaining adhesion of the first 110 and second 112 fastener portions of the bandage to the skin. Thus, placement of the bandage on the skin is maintained.

The dome structure 114 can be constructed from a variety of materials. For example, the dome can be constructed with a clear material for viewing the wound site. Alternatively, the dome structure can be constructed from an opaque material, so as to shield the wound site from view, for those who prefer not to view the site. The dome can also be constructed with a material that changes appearance to indicate infection. For example, some materials change color according to their temperature. A color change can thereby indicate the presence of increasing heat at the wound site, which can indicate infection in the wound area. Other materials that can be used for the dome structure might change appearance due to biological factors at the wound site, such as bacterial activity or in response to other infectious biochemical reactions. These materials and others (and combinations thereof) can be used for construction of the dome.

The gasket 116 is constructed of a stretchable material, such as a synthetic sponge material, and extends around the dome structure proximate the first fastener side edge 118, under the dome top edge 130, beneath the dome structure proximate the second fastener side edge 120, and beneath the bottom edge 132 of the dome structure. When the adhesive of the first fastener portion 110 and the second fastener portion 112 are removably adhered to a user's skin 105, the gasket 116 is held against the skin surface to form a seal against the passage of liquid, dirt, and contaminants. That is, the adhesive fastener portions 110, 112 hold the gasket 116 taut against the skin surface 105. When the user moves a limb or joint, the bandage might be effected by the distance between the first and second fastener portions changing. Because the distance between the pleats can change when they are unfolded, and because the gasket can stretch, the distance between the first and second fastener portions can increase without breaking the seal between the gasket and the skin surface. Thus, the sterile environment beneath the dome that is closed off by the gasket, is maintained intact. If desired, the bottom of the gasket 116 can be provided with a self-adhesive coating, to further encourage maintenance of the sterile seal. An adhesive gasket bottom would encourage maintenance of the sterile environment in situations where the distance between the first and second fastener portions is reduced with movement of limbs or joints.

The pleats 128, extending vertically up and down in the drawings, are fixed with respect to the distance between the top edge 130 and the bottom edge 132. Preferably, the relative dimensions of the fold spacing, the width of the first 110 and second 112 fastener portions, and the width of the dome structure 114, are such that the dome structure has a slight curve from one edge 130 to the other 132. Thus, the pleats impart an amount of rigidity to the dome structure, as the pleats comprise multiple arches in the dome structure. Thus, the dome structure 114 is sufficiently rigid to resist physical impact and abrasions from everyday activities and prevents such physical forces from being transferred to the wound site. In this way, the dome structure of the bandage 104 provides a protective shield for the underlying wound site, and in combination with the gasket 116 maintains the sterile environment.

Figure 3:
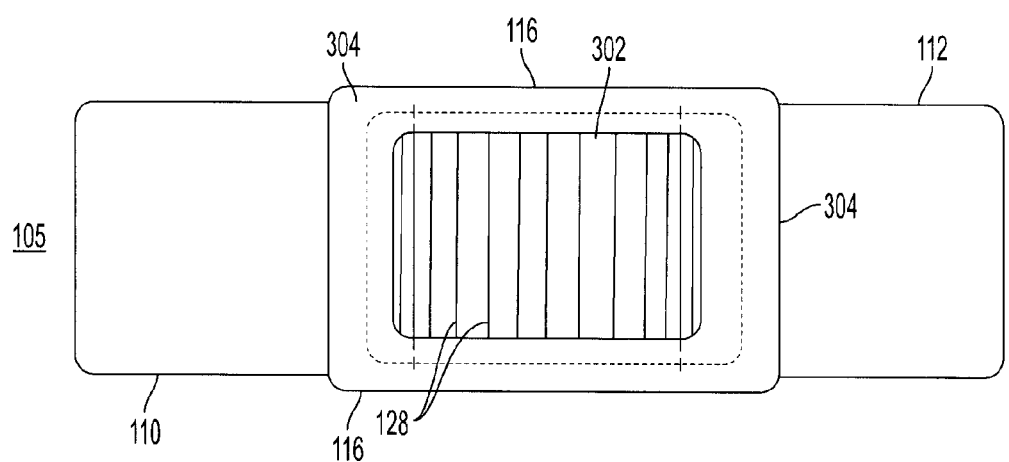
FIG. 3 is a bottom view of the FIG. 1 bandage in its contracted state.

FIG. 3 is a bottom view of the FIG. 1 bandage in its contracted state, prior to fastening to the skin surface. FIG. 3 shows the underside 302 of the dome structure 114, with some of the pleats 128 visible in this bottom view. The full extent of the gasket 116 is visible in the FIG. 3 bottom view illustration. As noted above, the underside of the gasket (the surface 304 that is visible in FIG. 3) can be provided with a self-adhesive coating to encourage maintenance of the seal between the gasket and the skin surface. The adhesive coating can comprise the same coating that is applied to the underside of the first 110 and second 112 fastener portions, such as removable adhesives used for conventional disposable bandages. In addition, either or both of the dome underside 302 and the gasket underside 304 can be provided with a medication or antiseptic coating or other substance or additive to promote health such as by improved healing and sterility. The underside 302 of the dome structure can be provided with a health-promoting substance in the form of a pad or medicated gauze or coating, as desired for the intended application. Contact should not occur between the dome and the wound site.

Figure 4:
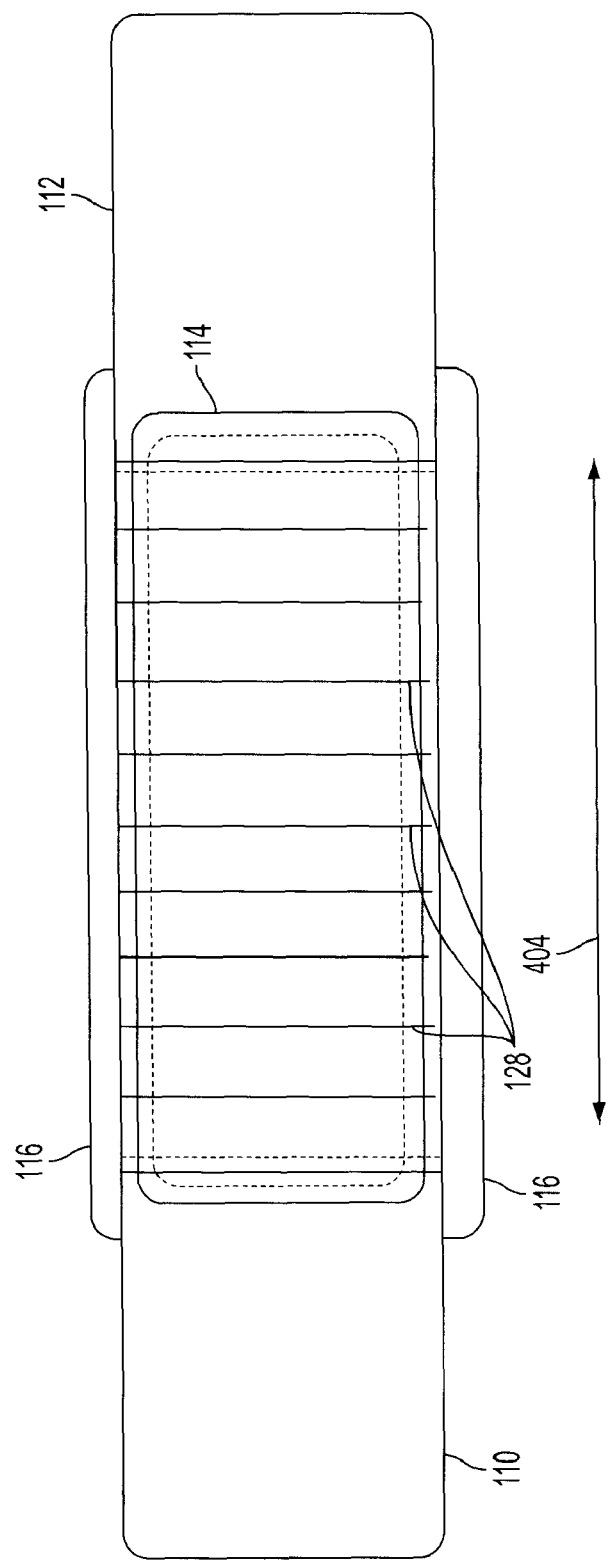
FIG. 4 is a top view of the FIG. 1 bandage in its deployed state.

FIG. 4 is a top view of the bandage 104 showing it in its deployed state, as contrasted with the compressed state shown in FIG. 2. FIG. 4 depicts how the bandage 104 would appear, for example, if the bandage was applied near a joint, and then after attachment the joint was bent or flexed. FIG. 4 indicates that the joint movement results in the first fastener portion 110 moving away from the second fastener portion 112 in the direction of the double headed arrows 404. FIG. 4 shows that the pleats 128 are moved further apart, as they become unfolded due to the fastener portions 110, 112 maintaining their grip on the skin, which has been stretched by the joint movement, so that the distance between the first portion edge 118 and the second portion edge 120 has increased from the compressed state of FIG. 2. It should be understood that the vertical lines 124 in the drawings represent peaks or valleys of the pleats in the dome structure. Hence, the number of pleats (vertical lines) has not changed from FIG. 2 to FIG. 4, but the spacing between the pleats has changed, as the fastener portions 110, 112 are pulled apart and the pleats are unfolded.

Figure 5:
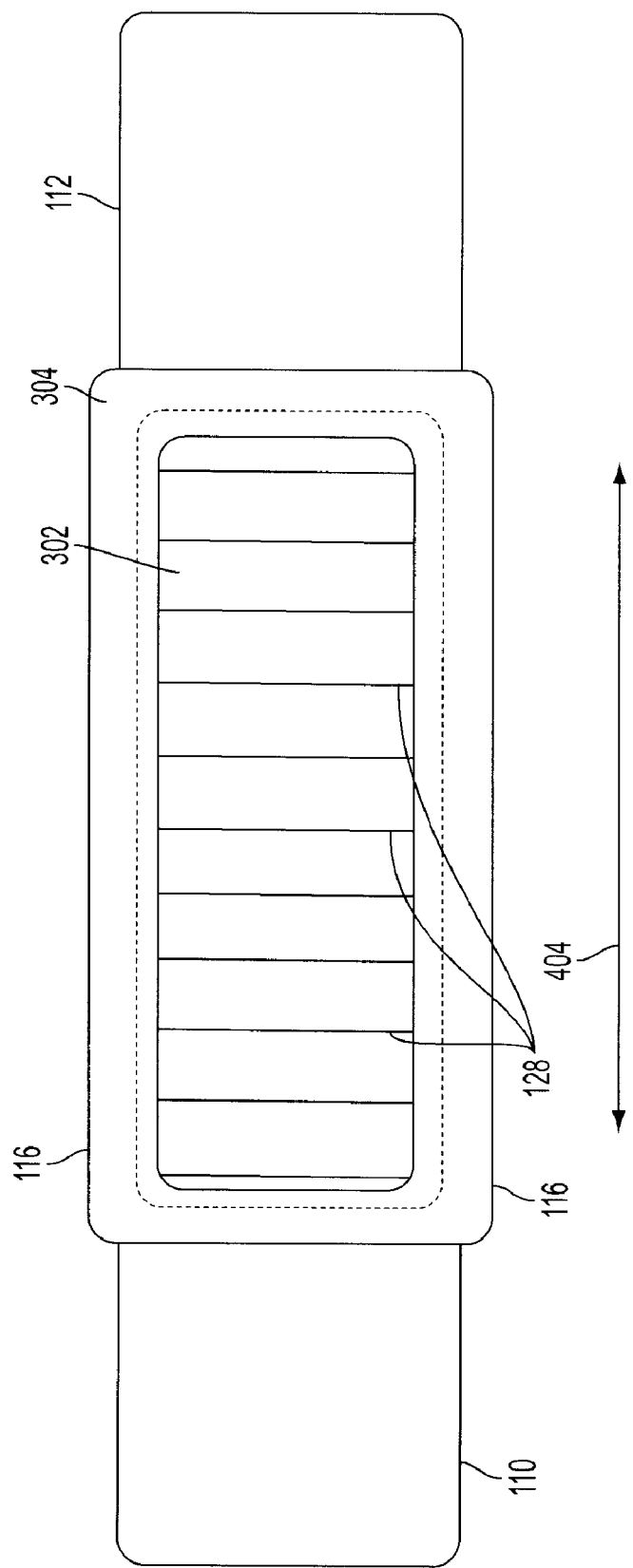
FIG. 5 is a bottom view of the FIG. 1 bandage in its deployed state.

FIG. 5 is a bottom view of the bandage 104 in its deployed state, corresponding to the underside of the FIG. 4 stretched condition. FIG. 5 shows that the gasket 116 has been stretched so that it is maintained in contact with the edges of the dome structure 114. As before, the spacing of the pleats 128 is increased from that shown in the compressed state of FIG. 2 and FIG. 3. Thus, the distance between the first fastener portion 110 and the second fastener portion 112 has increased, and the spacing between the peaks and valleys of the pleats 128 has increased, but the number of pleats remains unchanged.

Figure 6:
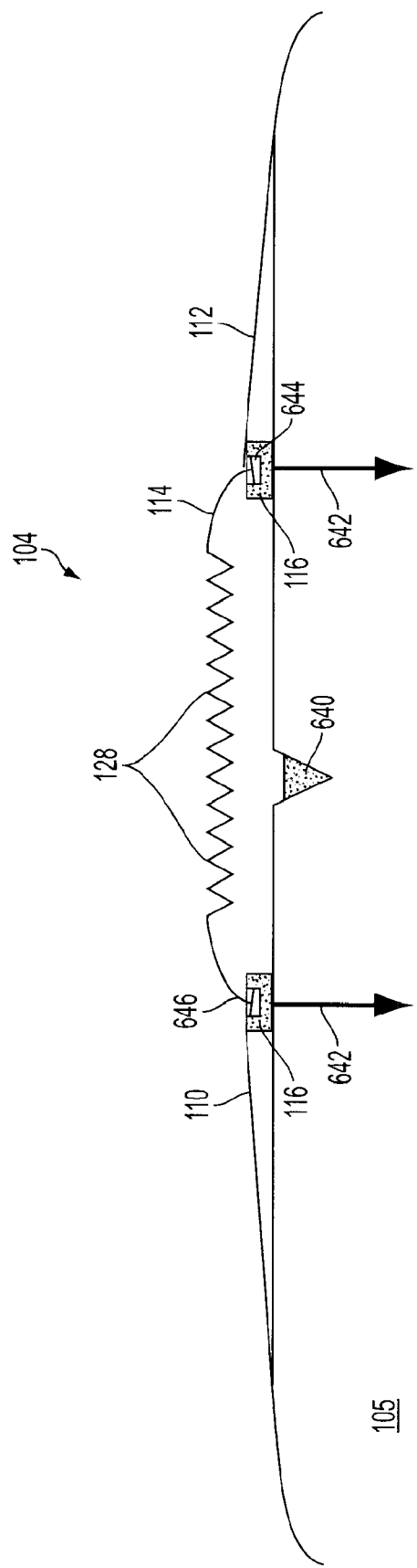
FIG. 6 is a cross-section view of the FIG. 1 bandage.

FIG. 6 is a cross-section view of the bandage 104 attached to the skin 105. The bandage 104 is shown in position over a wound site 640, with the dome structure 114 extending from the first fastener portion 110 to the second portion 112 and the gasket 116 encircling the underside of the dome structure to provide a sterile environment around the wound site. As noted above, the fastener portions 110, 112 can be pulled taut and removably fastened to the skin 105 so as to press the gasket 116 against the skin with a force applied in the direction of the arrows 642. Thus, when the skin 105 is stretched, as with movement of joints or limbs, the gasket 116 is maintained in contact with the skin and the sterile environment around the wound 640 is maintained. The gasket underside 304 (FIG. 3) can be provided with an adhesive coating to accentuate this effect.

FIG. 6 illustrates a construction detail demonstrating that the gasket 116 can be provided with a channel 644 that receives the bottom edge of the dome structure 114. The channel can provide an expedient manufacturing feature, making it easier to fasten the dome to the gasket and thereby reducing manufacturing costs. More particularly, the edge of the dome structure 114 can be provided with a lateral flange or lip 646. The flange provides increased area for the dome to make contact with the gasket and increases the security of the hold between the gasket and the dome. The flange 646 and the channel 644 can be provided independently of each other. That is, the dome structure 114 can be provided with a flange 646 even if there is no gasket channel 644, and the channel can be provided even if the dome has no flange.

The dome structure can be coupled or fastened to the first portion 110 and second portion 112 by a variety of means. For example, FIG. 7 shows detail from the channel-and-flange arrangement.

Figure 7:
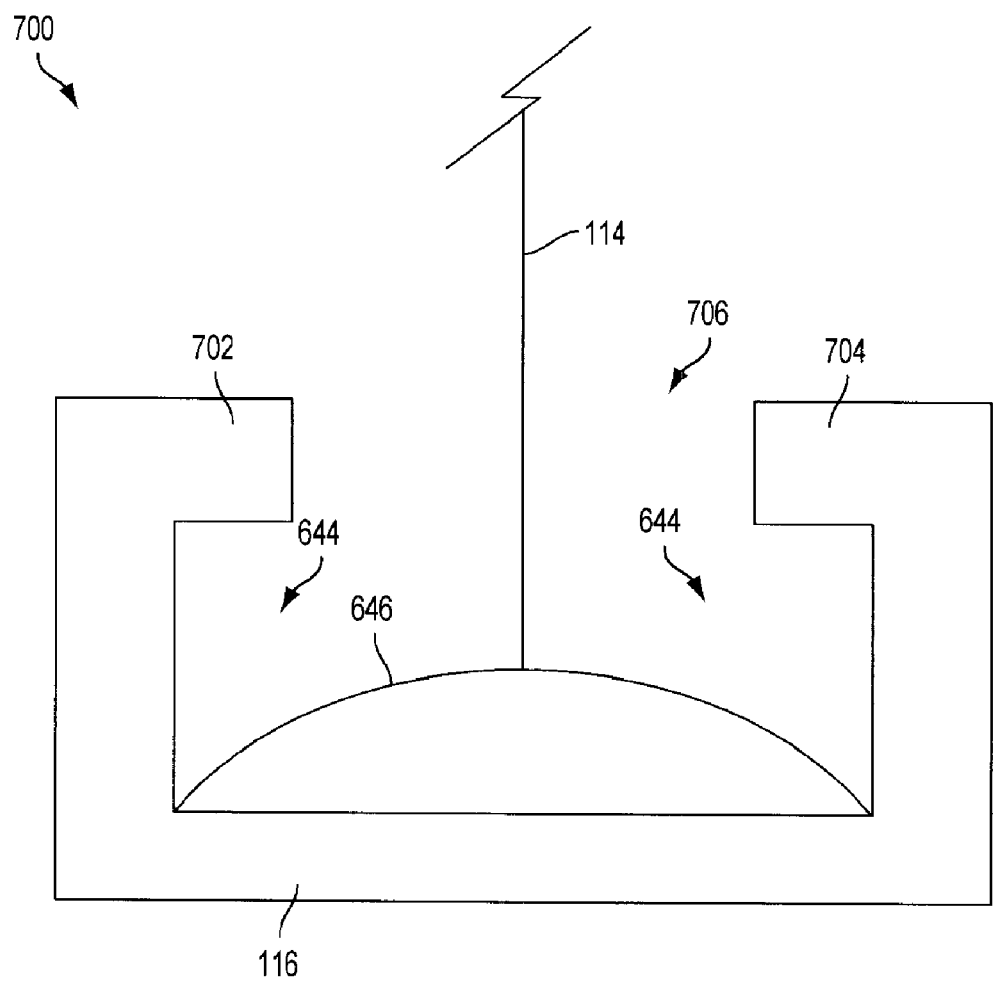
FIG. 7 shows detail from the channel and flange arrangement of FIG. 6.

FIG. 7 illustrates a bandage 700 in which the channel 644 receives the flanged end 646 of the dome structure 114. The flanged end is provided by a lateral protrusion or extension of the dome. The channel 644 is formed by paired overhangs 702, 704 in the gasket material 116 such that the channel 644 has an open roof 706 configuration. The flanged end 646 of the dome is sized so that it has greater width than the channel opening 706. The thickness of the flanged end is such that the flanged end has sufficient flexibility to flex and fit through the roof opening 706 and then seat within the channel 644. The flanged end 646 then resists pulling out of the channel 644 and tends to stay in place, even with stretching of the gasket 116 and movement of limbs.

FIGS. 8, 9, 10, and 11 show a construction of the gasket with a channel formed from a lip or single overhang.

Figure 8:
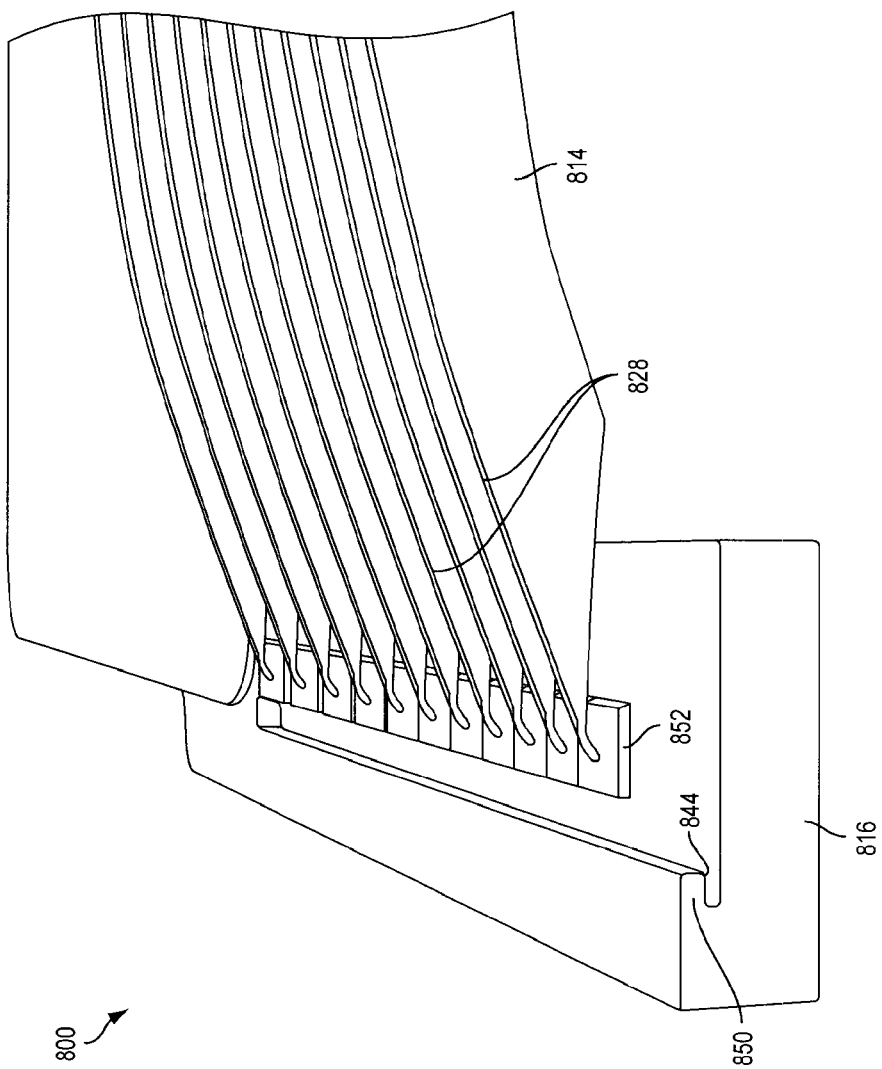
FIGS. 8, 9, 10, and 11 show construction of a wound guard bandage in which the gasket includes a channel formed from a lip or single overhang.
Figure 9:
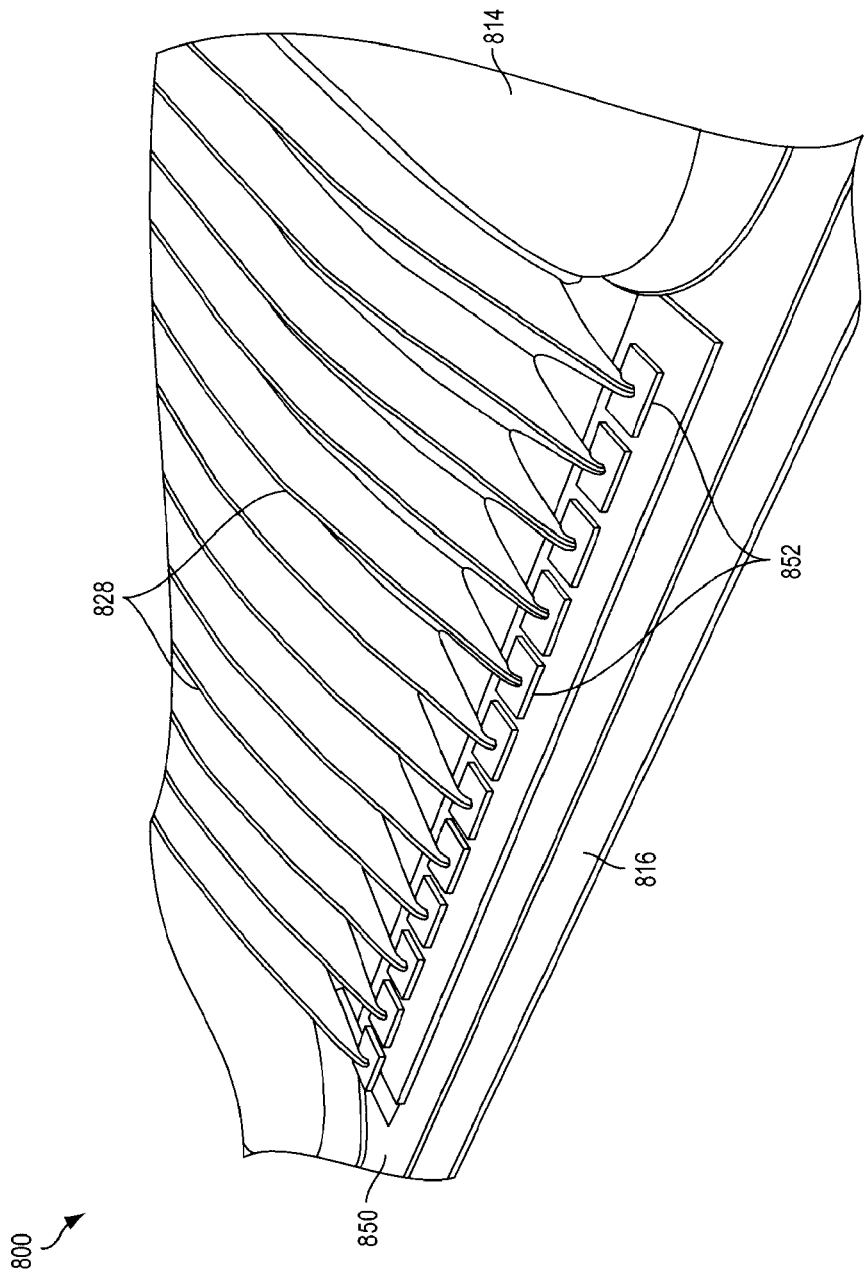

FIG. 8 shows a side perspective view of a wound guard bandage 800 with a channel 844 formed by an overhang 850 of gasket material 816. The dome structure 814 is formed with feet or pads 852 at the ends of the pleats 828. FIG. 9 shows another perspective view of the flange 850 and dome 814 with the pads 852, ready for insertion into the channel 844.

Figure 10:
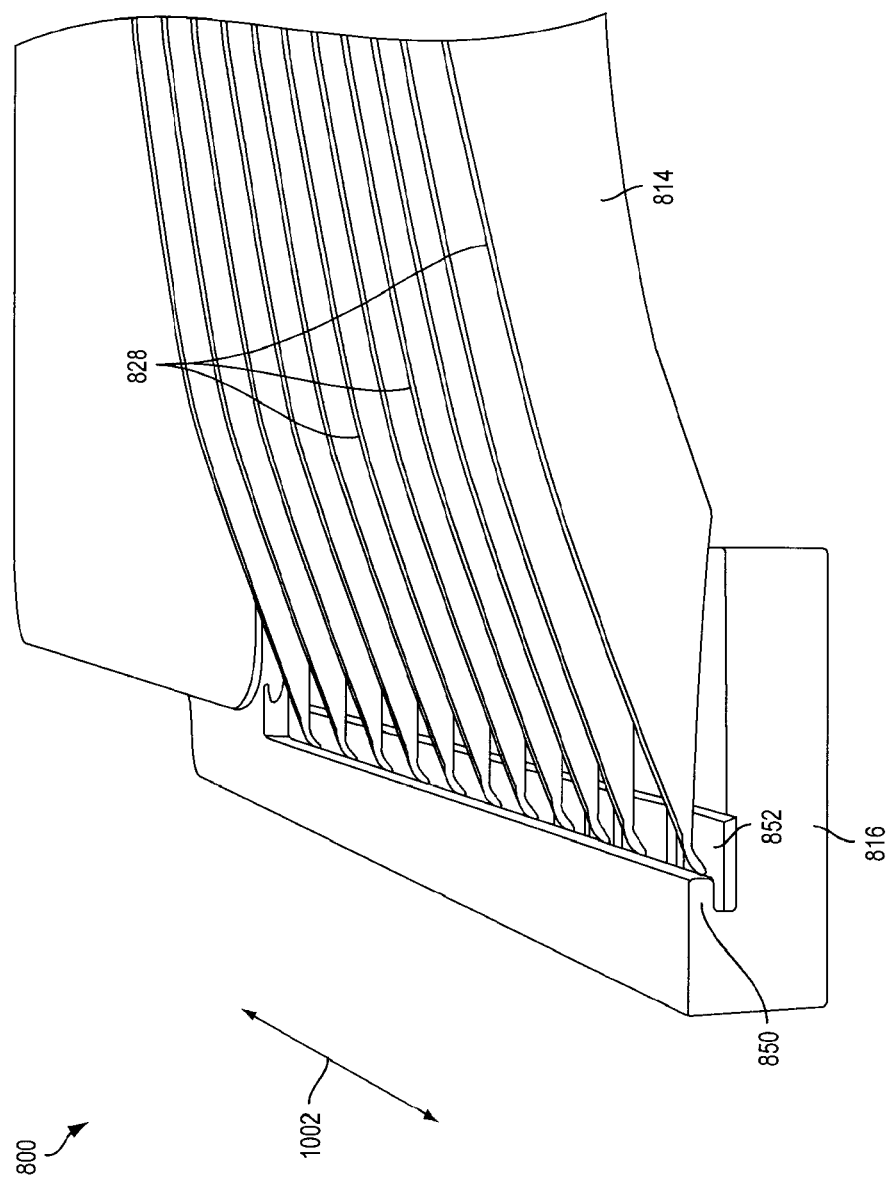

FIG. 10 shows that the ends of the pads 852 can slide beneath the overhang 850 of the channel 844 such that the pads resist being pulled out from the overhang. The dome structure 814 has sufficient flexibility that the dome can flex during production and permit insertion of the pads 852 into the channel overhang 850. Thereafter, the pads resist being pulled out. The pads can slide laterally in the direction of the arrow 1002, thereby maintaining the seal between the dome 814 and the gasket 816, and thereby maintaining the environment beneath the dome. Alternatively, the pads 852 can be fastened in place within the channel 844, such as by gluing or other bonding to the gasket channel. Fastening the pads in place is sufficient to ensure adequate flex of the dome structure to keep the wound area covered because the gasket 816 has sufficient stretch properties to permit flex between the pleats even without relative movement between the gasket and the pads 852 when the first and second portions 110, 112 (FIG. 1) are moved apart.

Figure 11:
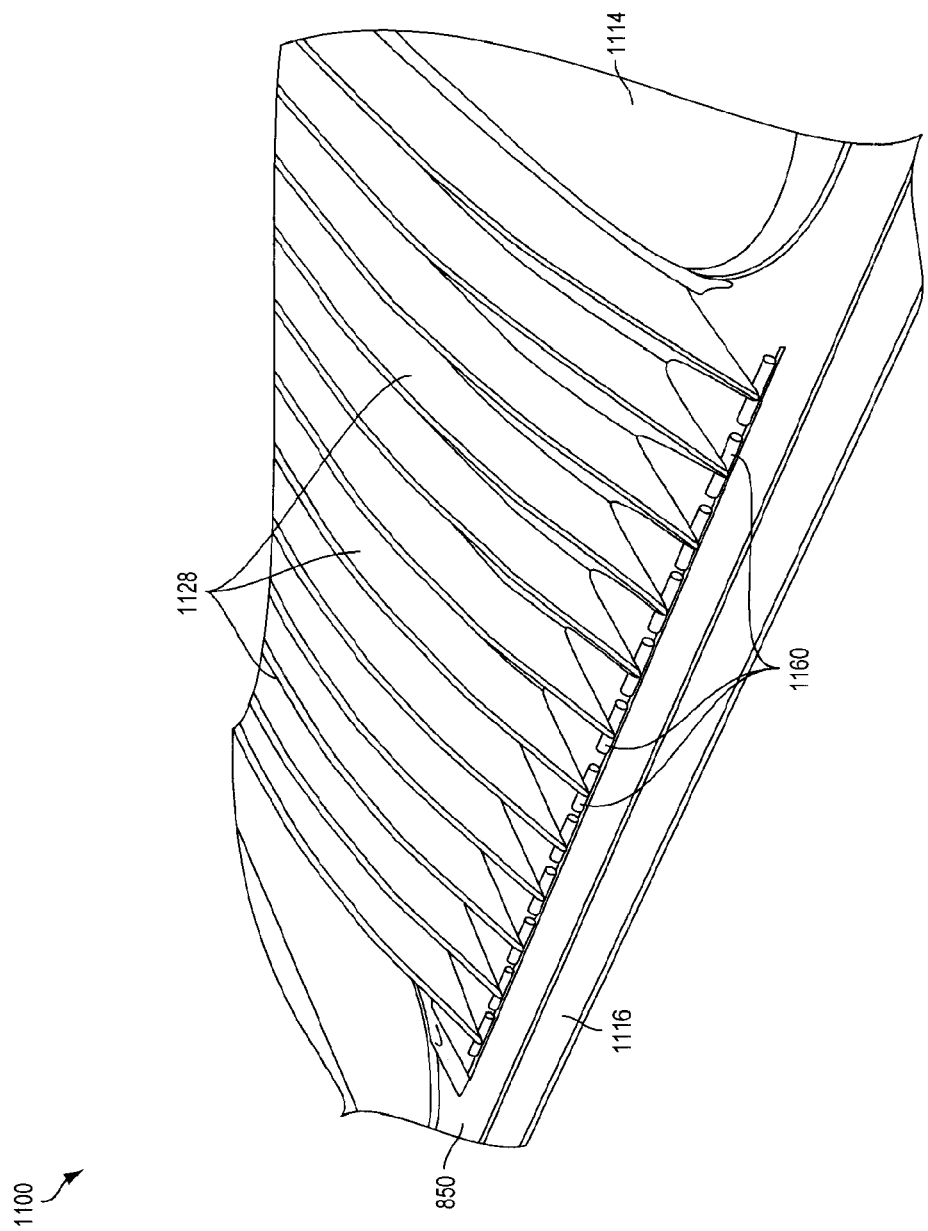

FIG. 11 shows an embodiment 1100 with a channel formed in the gasket 1116 that receives a dome structure 1114 having spaced apart cylinders or beads 1160 at the ends of the pleats 1128. The beads of the FIG. 11 embodiment have sufficient diameter that a portion of each bead will fit beneath the channel overhang 850 while resisting being pulled out. That is, as was the case with the FIG. 8, 9, 10 embodiment, the FIG. 11 dome structure 1114 has sufficient flexibility that the dome can flex during production and permit insertion of the beads 1160 into the channel overhang 850. Thereafter, the beads resist being pulled out.

Figure 12:
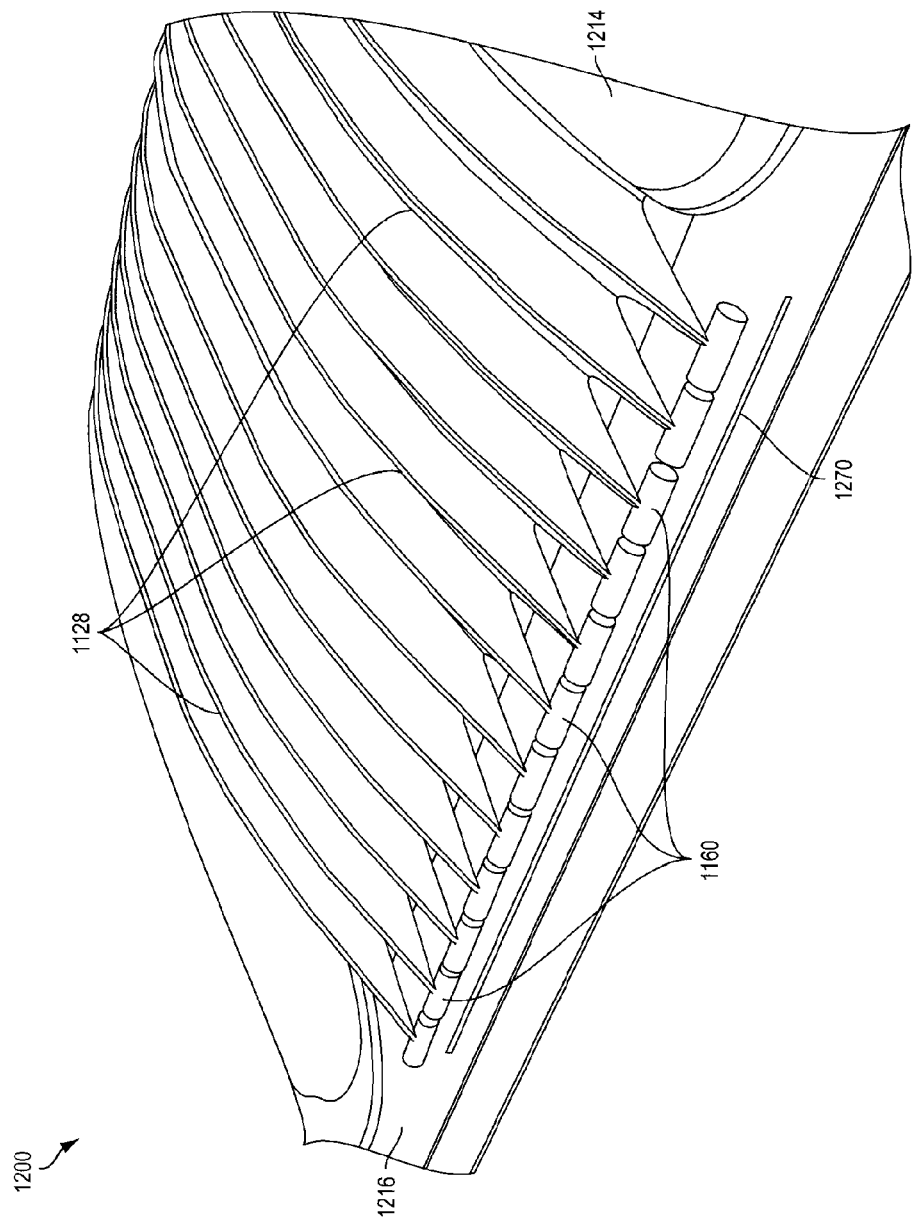
FIGS. 12 and 13 show construction of a wound guard bandage in which the gasket includes a slit forming a receiving channel for the dome structure.
Figure 13:
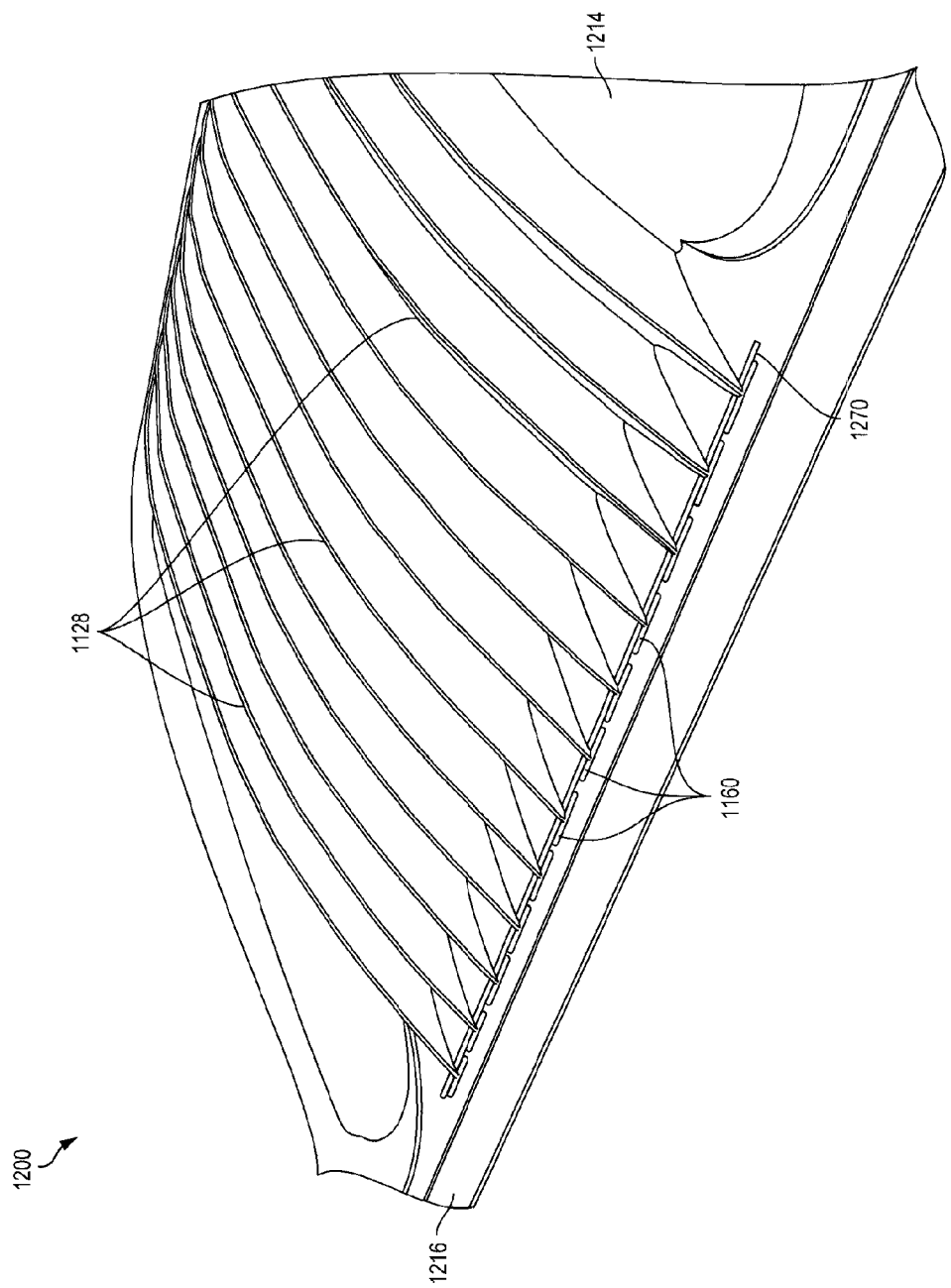

FIGS. 12 and 13 show a construction of the gasket with a slit in the gasket forming a receiving channel for the dome structure.

FIG. 12 shows a perspective view of the wound guard bandage 1200 with a slit 1270 formed in the gasket material 1216. The dome structure shown in FIG. 12 and FIG. 13 is formed with cylinders or beads 1160 like those illustrated in FIG. 11. Similarly, the beads 1160 of the FIG. 12, 13 embodiment have sufficient diameter that a portion of each bead will be received within the slit 1270 in the gasket 1216, which will partially close over the beads after insertion, and will resist being pulled out from the slit. That is, the dome structure 1214 has sufficient flexibility that the dome can flex during production and permit insertion of the beads 1160 into the channel slit 1270, while thereafter, the beads resist being pulled out. FIG. 13 shows the appearance of the wound guard bandage 1200 after insertion of the beads 1160 into the slit 1270 of the gasket 1216.

Figure 14:
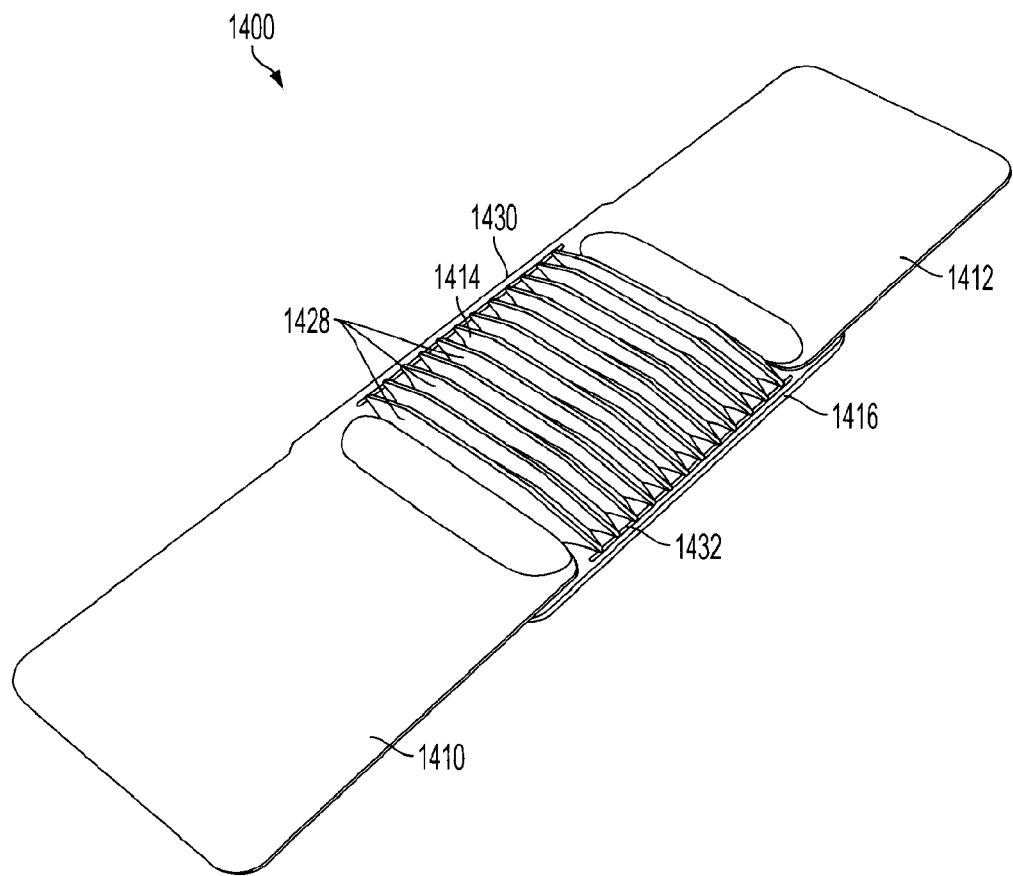
FIG. 14 is a perspective view of a wound guard bandage laid flat.

FIG. 14 is a perspective view of a wound guard bandage 1400 laid flat, showing the top or upper surface of the bandage. The bandage includes a first fastener portion 1410 and a second fastener portion 1412 that are attached laterally to a dome structure 1414. A gasket 1416 is provided around the underside of the dome structure. As described previously in connection with the other embodiments, the first and second fastener portions 1410, 1412 are provided with a self-adhesive coating on their underside, as is the case with conventional disposable self-adhesive bandage products, so that the self-adhesive coatings can be pressed against the skin surface of a user and so that the bandage can be removably fastened to the skin adjacent a wound area. When the adhesive portions of the bandage 1400 are pressed taut to the skin, the gasket 1416 is likewise pressed against the skin, and provides a sterile seal against the passage of liquid, dirt, and contaminants to the wound area. Only a few of the pleats are identified in FIG. 14 with a reference numeral 1428, for simplicity of illustration, but as with the illustrations of the other embodiments, it should be apparent that the pleats extend transversely across the dome structure from the top edge 1430 of the dome to the bottom edge 1432 of the dome, and are provided substantially along the lateral length of the dome structure 1414. The dome structure of FIG. 14 shows approximately twelve pleats 1428, but a greater or lesser number of pleats can be provided, depending on the size of the wound guard bandage, the intended application and environment of use for the bandage, and the material from which the dome structure is constructed.

Figure 15:
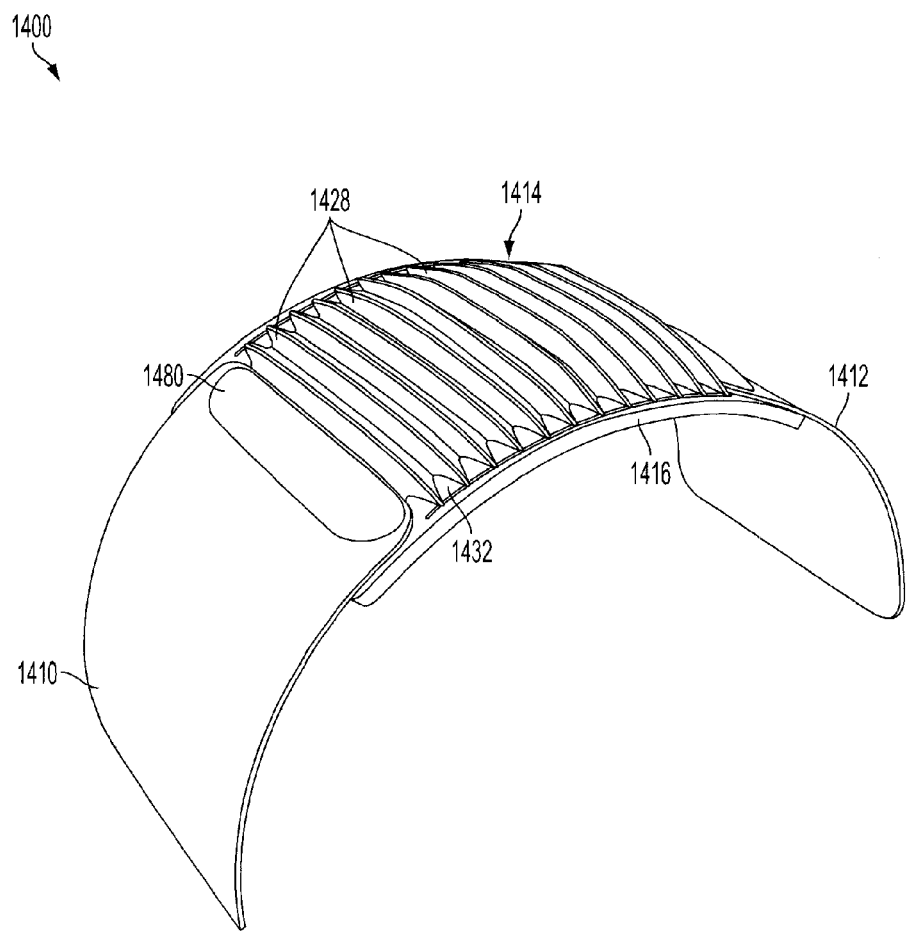
FIG. 15 shows the FIG. 14 bandage curved to illustrate the flex of the dome structure and gasket.

FIG. 15 shows the FIG. 14 wound guard bandage 1400 in a curved configuration to illustrate the flex of the dome structure 1414 and gasket 1416. One end of the first fastener portion 1410 appears to be raised 1480 because the portion of the dome structure 1414 covered by the first fastener portion 1410 at that location is itself raised, and the first fastener portion 1410 simply conforms to the raised dome structure. A similar circumstance applies to the second fastener portion 1412. FIG. 15 shows that the dome structure can be bent, or flexed, away from the laid flat position that is illustrated in FIG. 14. When the bandage 1400 is curved, such that the dome structure flexes by virtue of the pleats 1428, the gasket 1416 is sufficiently flexible so that it also flexes. FIG. 15 also shows that the dome structure 1414 itself remains in anchored in the gasket channel 1444 when the bandage is flexed. The dome remains anchored either by virtue of the ends of the dome pleats being retained in the channel 1444 by an overhang or similar structure, such as illustrated previously, or by virtue of the dome pleat ends being fastened or bonded to the gasket 1416, or a combination of the two.

Figure 16:
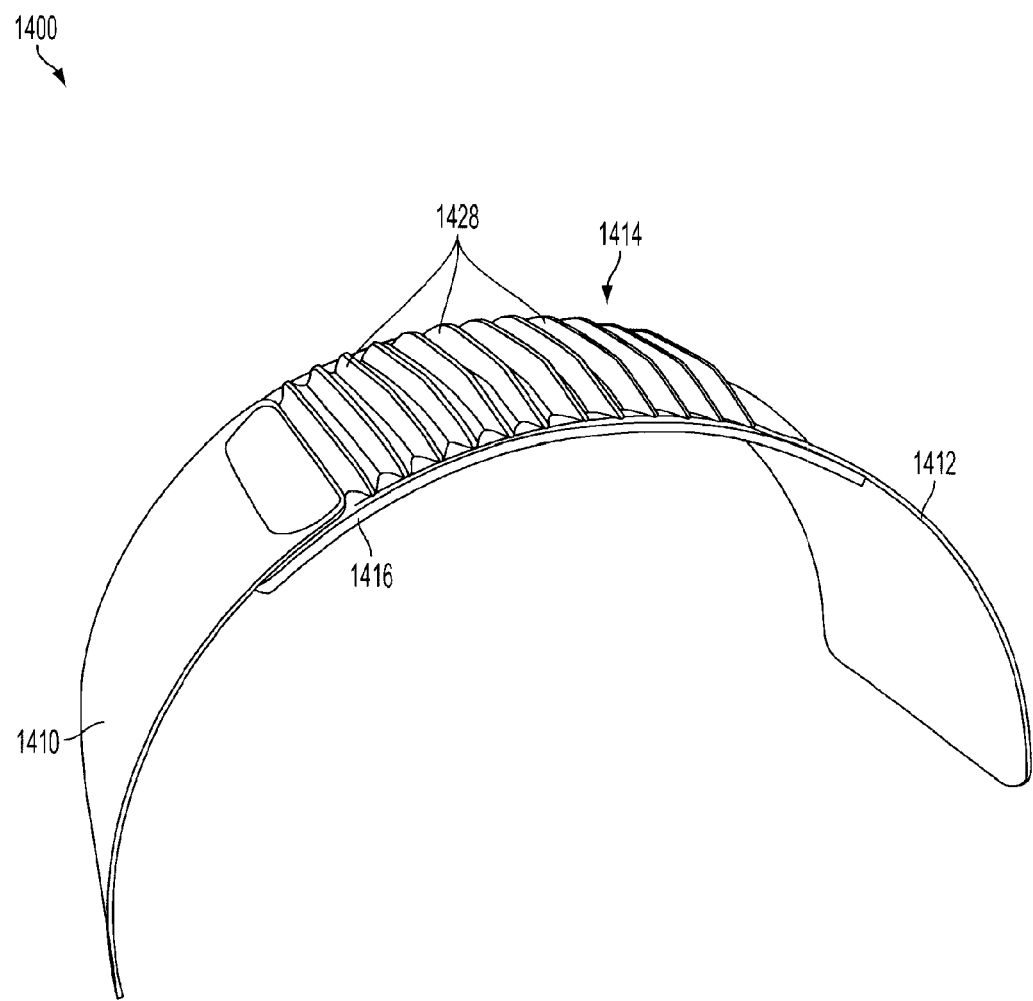
FIG. 16 shows the FIG. 14 bandage stretched laterally and curved to illustrate the flex of the dome structure and gasket.

FIG. 16 shows the FIG. 14 wound guard bandage 1400 stretched laterally and also curved, to better illustrate the flex of the dome structure 1414 and gasket 1416. In FIG. 16, it can be observed that the gasket 1416 has been stretched or flexed as compared to its configuration in FIG. 14 and FIG. 15. This stretched condition should be apparent by noting that the gasket 1416 in FIG. 16 has less thickness as compared with the condition of the gasket in FIG. 14 and FIG. 15. In general, the pleats 1428 in the expanded condition of FIG. 16 permit the dome structure 1428 to approximately double in length as compared to the contracted condition of FIG. 14 and FIG. 15. It should be understood, however, that other stretch proportions are possible, depending on the size of the pleats and the materials used in the construction of the gasket and the dome structure. Those skilled in the art will be able to make suitable selection of materials in accordance with the environment in which the wound guard bandage will be used, in view of the description herein.

Other modifications to the structures described herein are possible. For example, if desired, the dome structure such as described above can be constructed of a vapor permeable material so that airflow can be permitted over the wound area, but liquid passage into the sterile environment provided by the dome and the gasket is prevented. Vapor permeable materials generally comprise a microporous membrane having pores sufficiently large to permit passage of water vapor molecules and sufficiently small to block the passage of liquid water. Some commonly known vapor permeable materials that are suitable include materials manufactured under the trade name of "Gore-Tex"®. In this way, the healing process is not likely to be compromised by physical impacts and abrasions, and a reasonably sterile environment can be provided in which the healing progress can take place, resulting in faster healing and freedom from painful impacts and abrasions from everyday activities.

The dome structure can be constructed from an opaque material, or a clear (substantially transparent) material, or can be constructed with a material that changes appearance to indicate infection. Infection can be indicated, for example, by a material that changes color with temperature, to indicate rising heat at the wound site, which can be an indicator of infection. Other materials might respond directly to biochemical reactions to change their appearance and indicate the presence of infection. These materials and others (and combinations thereof) can be used for construction of the dome.

The dome structure can be provided with a medication or antiseptic lotion or other additive. Alternatively, a pad such as a gauze material can be located on the underside of the dome for containing a medication or antiseptic lotion or additive, to promote healing, reduce infection, and increase comfort. In any case, the gauze or other material or additive should be provided so as to not make contact with the wound site, so as to maintain a clear separation from the wound site and prevent becoming entangled with the healing tissue. Similarly, the gasket can be provided with medication or antiseptic lotions or other additives to promote healing, reduce infection, and increase comfort.

The wound guard bandage described herein provides a convenient means for maintaining a sterile environment around a wound site, so that the healing process is not likely to be compromised by physical impacts and abrasions, and a reasonably sterile environment can be maintained in which the healing progress can take place, resulting in faster healing and freedom from painful impacts and abrasions from everyday activities. The pleats in the dome structure provide sufficient flexibility to maintain a sterile environment over a person's wound site even as movement of the person occurs, and the pleats provide sufficient resistance to movement of the dome structure toward the wound site to provide protection against outside impacts directed toward the wound site. The packaging for the bandage can comprise sealed foil packs or other easily opened packs that maintain a seal against outside contaminants. The packaging can be provided with coding to indicate configurations with different sizes and different constructions.

The present invention has been described above in terms of presently preferred embodiments so that an understanding of the present invention can be conveyed. There are, however, many configurations for bandages not specifically described herein but with which the present invention is applicable. The present invention should therefore not be seen as limited to the particular embodiments described herein, but rather, it should be understood that the present invention has wide applicability with respect to bandages generally. All modifications, variations, or equivalent arrangements and implementations that are within the scope of the attached claims should therefore be considered within the scope of the invention.

I claim:

1. A disposable bandage for covering a wound area of a skin surface, the bandage comprising:
   a first fastener portion having an underside surface provided with a self adhesive;
   a second fastener portion having an underside surface provided with a self adhesive;
   a dome structure having a first side edge, a second side edge, a top edge, and a bottom edge, the dome structure coupled to the first fastener portion along the first side edge and coupled to the second fastener portion along the second side edge, and pleats that extend across the dome structure from the dome top edge to the dome bottom edge; and
   a gasket extending around the first side edge, top edge, second side edge, and bottom edge generally along a dome underside surface;
   wherein the gasket is held in contact with the skin surface and wherein a channel is formed in the gasket such that the edge of the dome can be received in the channel.

2. A bandage as defined in claim 1, further comprising a flange formed along the edge of the dome structure.

3. A bandage as defined in claim 2, wherein the dome structure includes a health-promoting substance.

4. A bandage as defined in claim 3, wherein the health-promoting substance is provided on the underside of the dome structure.

5. A bandage as defined in claim 2, wherein the gasket includes a health-promoting substance.

6. A bandage as defined in claim 2, wherein the dome structure is constructed from a clear material.

7. A bandage as defined in claim 2, wherein the dome structure is constructed from a material that changes appearance to indicate infection at the wound site.

8. A bandage as defined in claim 7, wherein the dome structure material changes color in response to changes in temperature.

9. A bandage as defined in claim 7, wherein the dome structure material changes color in response to an infectious biochemical reaction.

10. A bandage as defined in claim 1, wherein the dome is constructed from a vapor permeable material comprising a microporous membrane having pores sufficiently large to permit passage of water vapor molecules and sufficiently small to block the passage of liquid water.

11. A bandage as defined in claim 1, wherein the dome is provided with an additive that promotes healing and reduces infection.

12. A bandage as defined in claim 1, wherein the dome is constructed from a plastic material.

13. A bandage as defined in claim 1, wherein the dome is constructed from a pressed paperboard material.

14. A disposable bandage for covering a wound area of a skin surface, the bandage comprising:
   a first fastener portion having an underside surface provided with a self adhesive;
   a second fastener portion having an underside surface provided with a self adhesive;
   a dome structure having a first side edge, a second side edge, a top edge, and a bottom edge, the dome structure coupled to the first fastener portion along the first side edge and coupled to the second fastener portion along the second side edge, and including pleats that extend across the dome structure from the dome top edge to the dome bottom edge; and
   a gasket extending around the first side edge, top edge, second side edge, and bottom edge;
   wherein the gasket is held in contact with the skin surface;
   wherein the upper surface of the gasket includes an open channel that receives the dome structure.

15. A bandage as defined in claim 14, wherein the dome structure is fixed against movement relative to the gasket.

16. A bandage as defined in claim 15, wherein the dome structure is bonded to the gasket.

17. A bandage as defined in claim 14, wherein the dome structure moves relative to the gasket.

18. A bandage as defined in claim 14, wherein the dome structure includes flanged extensions that are received into the open channel.

19. A bandage as defined in claim 14, wherein the dome structure includes beads along the edges of the dome structure extending between the first portion and the second portion.

20. A bandage as defined in claim 14, wherein the upper surface of the gasket includes a slit that receives the dome structure.

21. A bandage as defined in claim 14, wherein the open channel is formed from an overhang on the upper surface of the gasket.

22. A bandage as defined in claim 14, wherein the open channel is formed from opposed overhangs of the gasket.

23. A bandage as defined in claim 14, wherein the dome structure includes a health-promoting substance.

24. A bandage as defined in claim 14, wherein the gasket includes a health-promoting substance.

* * * * *